(12) United States Patent
Avci (10) Patent No.: US 10,444,127 B2
(45) Date of Patent: Oct. 15, 2019

(54) BIYO TRAP

(71) Applicant: Recep Avci, Bozeman, MT (US)

(72) Inventor: Recep Avci, Bozeman, MT (US)

( * ) Notice: Subject to any disclaimer, the term of this patent is extended or adjusted under 35 U.S.C. 154(b) by 251 days.

(21) Appl. No.: 14/700,130

(22) Filed: Apr. 29, 2015

(65) Prior Publication Data

US 2016/0320277 A1    Nov. 3, 2016

(51) Int. Cl.
*G01N 1/40* (2006.01)
*C12Q 1/24* (2006.01)
*G01N 33/569* (2006.01)

(52) U.S. Cl.
CPC .......... *G01N 1/405* (2013.01); *C12Q 1/24* (2013.01); *G01N 33/569* (2013.01); *G01N 2001/4038* (2013.01); *G01N 2001/4088* (2013.01)

(58) Field of Classification Search
None
See application file for complete search history.

(56) References Cited

U.S. PATENT DOCUMENTS

| | | | | |
|---|---|---|---|---|
| 4,036,698 A * | 7/1977 | Bush | ................. | C12Q 1/22 435/287.4 |
| 5,741,662 A * | 4/1998 | Madsen | ........... | G01N 33/56911 435/34 |
| 6,565,749 B1 * | 5/2003 | Hou | ................. | A61L 2/0017 210/263 |
| 6,855,490 B2 * | 2/2005 | Sompuram | ...... | G01N 33/54386 435/4 |
| 2003/0168401 A1 * | 9/2003 | Koslow | ................. | A61L 2/0017 210/500.25 |
| 2005/0029195 A1 * | 2/2005 | Gibson | ................. | B01J 20/14 210/656 |
| 2011/0006009 A1 * | 1/2011 | Hamlin | ................. | A01N 25/34 210/668 |
| 2012/0241391 A1 * | 9/2012 | Carlson | ................. | A01N 25/10 210/808 |

OTHER PUBLICATIONS

Anderson et al., Functional PEG-Modified Thin Films for Biological Detection, Langmuir, 2008, 24 (5), pp. 2240-2247.*

* cited by examiner

*Primary Examiner* — Andrea S Grossman
(74) *Attorney, Agent, or Firm* — US IP Attorneys, P.C.; Timothy Marc Shropshire (57) ABSTRACT

A device consisting activated microfibers, such as glass and cellulose, comprising the 3D network, packed in small volumes, traps and concentrates the bacteria from trace contaminated liquids rapidly. It functions for concentrating and rapid detection of microbes in <20 min. The device enables the easy recovery of concentrated bacteria, which involves the mixing and agitation of the contaminated sample, followed by the suction. The chemistry of the system involves coupling aminosilane groups such as 3-aminopropyl methyldiethoxysilane (APMDES) or carboxylated groups in 3-triethoxysilyl propylsuccinicanhydride (TESPSA) to the —OH bearing moieties on the surfaces of glass and/or cellulose microfibers, attained by solution or vapor phase techniques. The device has a wide variety of applications, including rapid detection of trace bacteria in contaminated liquids; in vegetable, fruit, meat, tabletop and countertop wash-offs; and in the filtration of liquids (water or fuels) to remove bacteria or other microorganisms.

6 Claims, 5 Drawing Sheets

BIYO TRAP

CROSS REFERENCE TO RELATED APPLICATIONS

Not applicable.

FEDERALLY SPONSORED RESEARCH AND DEVELOPMENT

Not applicable.

MICROFICHE APPENDIX

Not applicable.

BACKGROUND OF THE INVENTION (1) Field of the Invention

The present invention relates to a method used as a preparatory step in the qualitative and quantitative analysis of liquid samples, and is particularly valuable when the substance to be determined is present in trace amounts. The invention also relates to a device for carrying out the method. By using the method and the device according to the invention, even small amounts (~1 cell/ml) of microorganisms can be determined rapidly in liquid samples.

(2) Background of Invention

Most waterborne human pathogens cause infections and human disease via the ingestion of feces-contaminated water or food. Various human parasites and pathogens are transmitted via the human fecal contamination of water used for drinking, bathing, recreation, or washing/preparation of foods. To ensure good public health, there is a need for readily available methods to detect and enumerate trace pathogens in water rapidly (<1 hr).

While the presence of pathogens in water presents a significant public health concern, the recovery of pathogens from environmental samples is generally difficult. Many fecal pathogens are infective at densities so low that water sample collection and concentration is inconvenient. Also, unpredictable physiological and morphological changes are observed in these pathogens in response to nutrient limitations and environmental stressors, and these injuries cause the organisms to exhibit atypical reactions.

These organisms then require specialized handling for their resuscitation. In addition to pathogens, viable but uncultivable organisms may be present in the water sample.

The methods commonly used to detect these pathogens were initially designed for clinical, rather than environmental, samples. However, clinical isolates are usually provided an ideal environment in which needed nutrients as well as protection from harsh environmental conditions, such as cold, heat, damaging chemicals, and radiation, are readily supplied to the isolate. In contrast, environmental isolates are exposed to harsh environmental conditions and effectively compete with organisms naturally present and adapted to life in the environment.

Pathogenic organisms are rarely readily adaptable to prolonged survival in the environment. For this reason, fecal microbial water contamination is often assessed by testing for harder and more robust, but not necessarily pathogenic, microbes, referred to as indicator organisms, such as the coliforms, especially *Escherichia coli*, and *Enterococcus* species. Indicator organisms serve to indicate whether a given water supply may be generally contaminated with fecal material without actually testing for the presence of all enteric pathogens. This contamination is viewed as predictive of the potential presence of enteric pathogens (i.e., without the presence of fecal material, the chances of these indicator organisms being present are usually remote).

In water quality inspection, it is essential to detect both the types of bacteria in the water being tested and the number of bacteria included in a given unit quantity of the water. Detection of the number of bacteria in water is absolutely necessary for super-pure water, such as is required in manufacturing medicines, in which the number of bacteria must be limited to an extremely small value, or in the case of manufacturing semiconductor devices (especially super-LSI semiconductor devices), in which the number of bacteria per 10 cc of super-pure water is limited to ten or less.

In a conventional method of detecting the number of bacteria in a unit quantity of super-pure water, a sample of the water is extracted and the bacteria in the sample are cultivated to allow them to multiply. The bacteria thus treated are then filtered and stained, and the stained bacteria are counted under a microscope.

When such a detecting method is employed, it takes about seven days to accomplish all of the steps, from sampling the super-pure water to counting the bacteria. If the quality of super-pure water is thereby determined unacceptable, semiconductor devices manufactured during the detection period must be discarded, which increases the average manufacturing cost of the devices.

The present inventors have proposed a bacteria counter that can detect the number of trace bacteria in water in an extremely short period of time, with the result that the manufacturing cost of semiconductor devices or the like can be reduced.

A need exists for a device or a system that solves the issues described above. The present invention fulfills those needs.

It is an objective of the invention to overcome or alleviate a problem of the prior art.

BRIEF SUMMARY OF THE INVENTION

One objective of the various disclosed embodiments in the present invention is to provide an appliance for concentrating and detecting bacteria in the provided samples.

Preferably, the methods and apparatuses address, or at least ameliorate, one or more of the problems described above. To this end, the present invention, related to the use of effectively concentrating bacteria and with some other unique aspects, is disclosed.

Accordingly, it is a primary objective of the present invention to provide a handheld device that includes: a filtration system, an optical base detection system, and a data processing and display system.

In one aspect, the present invention provides an activated 3D fiber network that is composed of glass or cellulose microfibers and packed in small volumes with inlets and outlets to hoses, which are able to pump trace-contaminated liquid samples.

In another aspect of the present invention, the system allows for the fast capturing and concentration of bacteria through the large, connected 80-90% porous voids in the 3D fiber network.

In a further aspect, the activated network of 3D fibers possesses a covalently coupled monolayer of positive or negative charge throughout the 3D network.

It is another objective of the present invention to provide easy recovery of viable or dead bacteria via the process of mixing, agitation, centrifuging if necessary, and suction with a pipette or a small syringe.

It is another objective of the present invention to provide concentrated DNA associated with the concentrated bacteria and eukaryotic microorganisms for qPCR and/or genomic analysis.

It is another objective of the present invention to concentrate loose DNA for qPCR and/or genomic analysis.

It is another objective of the present invention to make use of the concentrated ATP associated with the concentrated bacteria for rapid detection via ATP-activated bioluminescence.

In yet another aspect, the captured bacteria can be washed off, and the remaining original medium can be replaced with the desired liquid medium or buffer without affecting the viability of the trapped bacteria.

It is still another objective of the present invention to provide a novel idea that involves the combination of silane chemistry, a known activation chemistry, and attaching charged molecules covalently to the surface of the 3D porous network of a fiber material such as glass. The whole process allows one to trap and concentrate microorganisms rapidly, even in a high salinity environment. This is due to recognition (by the inventor) of the fact that the collective motion of the charges on the bacteria surface sweeps away the individual small ions in the solution near the oppositely charged surfaces of the microfibers.

In accordance with the invention, one aspect of the present invention involves the aminosilanes or other silanes of interest. The surface modification can be attained through solution or vapor phase techniques, depending upon the silanes, formerly mentioned.

In a further aspect, the charged 3D networks of microfibers disclosed in the present invention are robust and are composed of inert surfaces. The microfibers tend to stay charged, even in harsh chemical environments. The monolayer of a charged silane group prevents other organics from physical adsorption or chemisorption on the surface of these fibers, enabling charged activity for a long period of time. It has been observed that amine groups are detrimental to the viability of some species of trapped bacteria but not all, though this has no effect on the recovery of the DNA and the ATP associated with the trapped bacteria (dead or alive).

ATP-activated bioluminescence has been utilized as a rapid detection assay with the invention. Furthermore, X-ray photoelectron spectroscopy (XPS) has verified the surface monolayer properties of the modified microfibers, and zeta potential measurements have verified the charge concentrations on the microfibers. The limit of detection and loose DNA concentration have been verified using qPCR. A conventional fluorometer (Qubit®2) is used to confirm the current limit of detection without employing a bacteria (or DNA) concentrator. The use of BiyoTrap consistently improves the detection limits of conventional sensors by more than 3-4 orders of magnitude within a short time.

Additionally, the present invention provides a device that has a significant potential for commercialization in the food industry, along with biomedical and public health applications.

Briefly, the present invention effectively traps and concentrates bacteria nonspecifically and rapidly, and has the potential to capture them specifically. It also has potential to concentrate loose DNA nonspecifically. The present invention provides a handheld commercial device at a reasonable cost.

Other aspects of the present invention will become apparent from time to time throughout the specification, as hereinafter related.

In this respect, before explaining at least one embodiment of the invention in detail, it is to be understood that the invention is not limited in its application to the details of construction and to the arrangements of the components set forth in the following description or illustrated in the drawings. The invention is capable of other embodiments, and of being practiced and carried out in various ways. Also, it is to be understood that the phraseology and terminology employed herein are for the purpose of description, and should not be regarded as limiting.

These, together with other objectives of the invention and the various features of novelty that characterize the invention, are pointed out with particularity in the disclosure. For a better understanding of the invention, its operating advantages, and the specific objectives attained by its uses, reference should be had to the accompanying drawings and descriptive matter, in which there are illustrated preferred embodiments of the invention.

BRIEF DESCRIPTION OF THE SEVERAL VIEWS OF THE DRAWINGS

To further clarify various aspects of some example embodiments of the present invention, a more particular description of the invention will be rendered by reference to specific embodiments thereof, which are illustrated in the appended drawing. It is appreciated that the drawing depicts only illustrated embodiments of the invention and is therefore not to be considered limiting of its scope. The invention will be described and explained with additional specificity and detail through the use of the accompanying drawing in which.

DETAILED DESCRIPTION OF THE INVENTION

Various aspects of the illustrative embodiments will be described using the terms commonly employed by those skilled in the art to convey the substance of their work to others skilled in the art. However, it will be apparent to those skilled in the art that the present invention may be practiced with only some of the described aspects. For purposes of explanation, specific numbers, materials, and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

The disclosed embodiment of the present invention is to provide a handheld or desktop specialty appliance that functions for concentrating and detecting bacteria in the provided samples. The present invention is a device, made up of activated microfibers, such as glass or cellulose, which traps and concentrates the bacteria from trace contaminated liquids rapidly.

The device that facilitates the rapid detection of microbes in <20 min is disclosed herein. It also has the potential to identify the pathogens from the contaminated liquids.

Referring to the drawings, a first preferred embodiment related to the BiyoTrap and its various components, thereof, according to the invention, is described herein. The various aspects with the related figures have been summarized already.

Figures 1A, 1B, 1C:
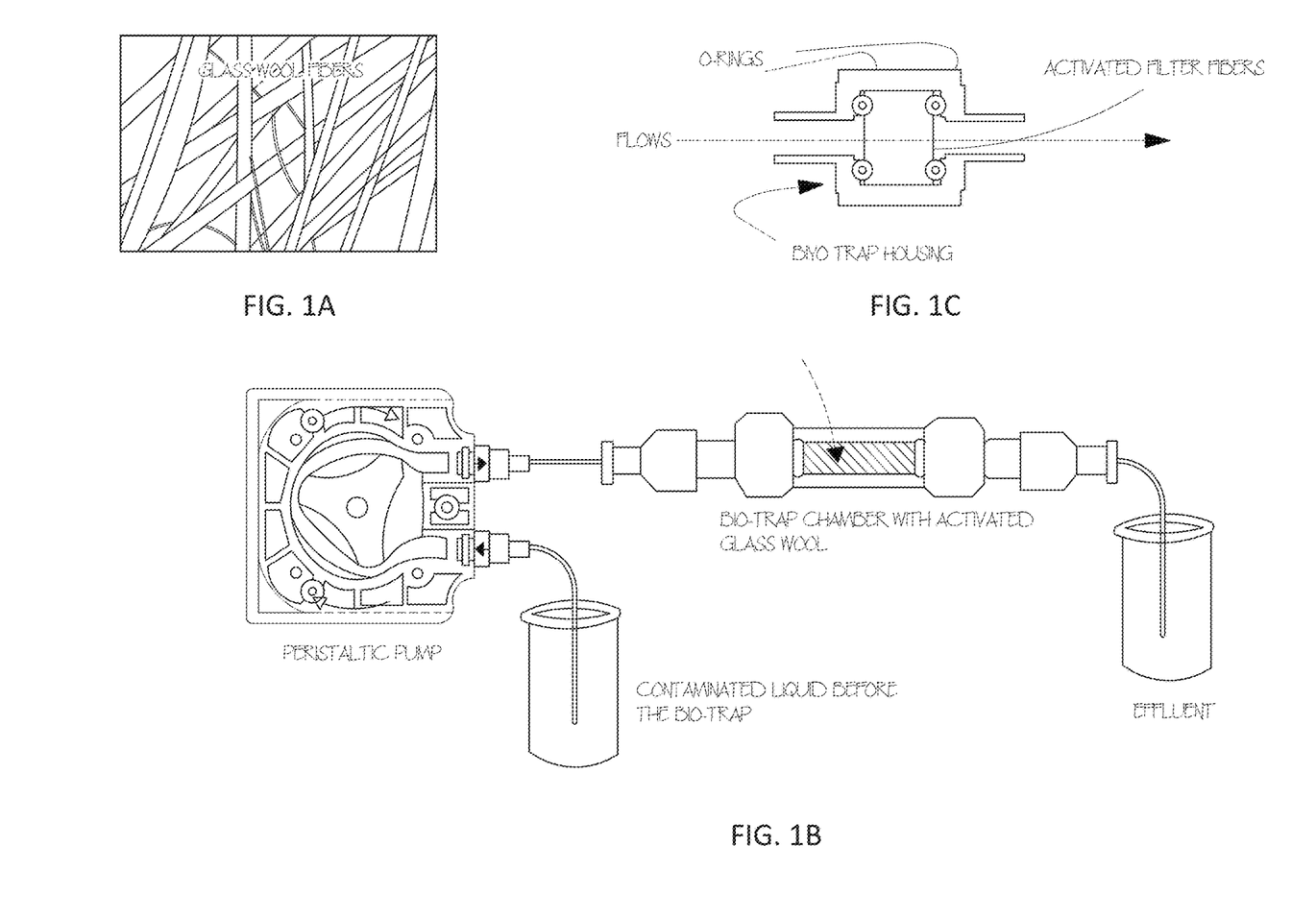
FIG. 1A is an image of glass microfibers through a scanning electron microscope, according to the preferred embodiment of the present invention.
FIG. 1B is a schematic representation of the BiyoTrap setup, according to the preferred embodiment of the present invention.
FIG. 1C is again a schematic representation of the alternative assembly of the BiyoTrap.
Figure 6:
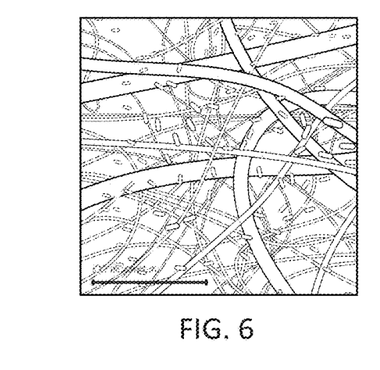
FIG. 6 is a microscopic image of *E. coli* bacteria trapped in activated glass wool fibers and polymer fibers, according to the preferred embodiment of the present invention.

In FIG. 1A, a microscopic image of the glass wool fibers is represented. The basic concept of the present invention involves a 3D network of activated microfibers that are composed of glass or cellulose and packed in a small volume. Specifically, a BiyoTrapped bacterial colony of *E. coli*, under confocal microscopy, is shown by FIG. 6. The activated microfibers are the glass wool fibers (thin fibers), but not the polymer fibers (thick fibers), as suggested by the lack of trapped bacteria in the immediate vicinity of these thick fibers.

In accordance with the invention, the inlets and outlets connected to hoses that pump trace contaminated liquid through the BiyoTrap medium are represented in FIG. 1B. The BiyoTrap, in accordance with the present invention, is shown in a schematic format (FIG. 1B) to more clearly illustrate the components thereof.

FIG. 1C again represents a schematic format of the BiyoTrap, which depicts the alternative assembly of its components using a stack of activated filter fibers. A BiyoTrap can also be assembled as layers of activated 3D fiber filters in a filter housing.

In another preferred embodiment, the present invention illustrates the fast capturing and concentration of bacteria. As the contaminated liquid is pumped through the 3D activated BiyoTrap medium, the large connected voids, with ~80-90% porosity in the 3D fiber network, allow a rapid flow of the contaminated liquid through the 3D filter network. At the same time it traps the charged bacteria with the efficiency of a ~0.2-μm filter, allowing only liquid free of bacteria and other uncharged entities to pass through the BiyoTrap network.

The present invention, in another preferred embodiment, also allows the easy recovery of concentrated bacteria or genetic material. The process involves mixing, if necessary adding a small amount of liquid, and agitation followed by suction with a pipette or a small syringe. For DNA and/or ATP assays the appropriate reagents can be mixed directly into the BiyoTrap 3D matrix, followed by standard procedures. This is perhaps not the best or most efficient way to recover bacteria, but it is the most practical way to recover most of the most bacteria from the BiyoTrap and it is definitely the best way to recover almost all the genetic material. To recover bacteria from the BiyoTrap medium, as shown in FIG. 1B, if the volume is ~1 ml it would be advisable to simply pipette the concentrated solution from the trap. Recovering bacteria from very small BiyoTrap volumes (~200-300 μL as in FIG. 1C) requires immersing the fibers with the concentrated bacteria in a 200-300-μL TRIS buffer solution followed by mixing, agitation, and pipetting. This approach dilutes the BiyoTrap concentration by a factor of two, but enables the recovery of the majority of the bacteria (including the genetic material and the ATP) from the filter medium.

The inventive process also allows the washing of those captured bacteria which are immune to the biocidal effects of amine groups attached to the glass fibers, wherein the original medium can be replaced with the desired liquid medium or buffer without affecting the viability of the BiyoTrapped bacteria for use in further studies.

Figure 4:
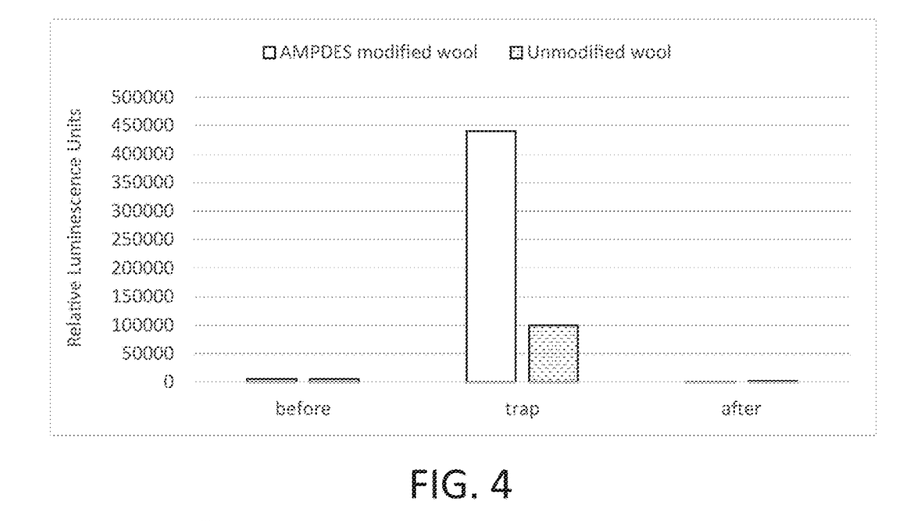
FIG. 4 is a graphical representation of the trapping experiment, with *Marinobacter* in seawater, comparing activated and inactivated glass fibers.

Most microorganisms and DNA have a distribution of negative charge over their surfaces. However, the literature also cites a handful of positively charged bacterial surfaces. According to the preferred embodiment of the present invention, the activation of a fiber network is the laying down of a monolayer of positively or negatively charged but chemically nonreactive stable molecules on the surfaces of these microfibers such that the charge will remain stable over a wide range of salinity and harsh chemical conditions. Furthermore, the charged molecules must be coupled to the surfaces of glass or other microfibers covalently and should remain stable over a wide range of pH>6, salinity, and harsh chemical environments. A lower pH may jeopardize silane bonding between the charged molecule and the solid surface. The charged molecules should be stable and nonreactive with the environment, maintaining a positive/negative charge cloud over the surfaces of the 3D fiber network. The electrostatic coulomb attraction between the surfaces of the microorganisms and the surface charge clouds distributed throughout the activated 3D network of the microfibers traps the bacteria near the surfaces of this 3D fiber network. Typically, bacteria, loose DNA and fungi have negatively charged surfaces; hence, if the fibers are charged positively, they will be trapped inside the porous voids of the 3D fiber network, close to the surfaces of the charged fibers. In the case of a negatively charged 3D network, negatively charged microorganisms will be repelled by the fiber network, will be concentrated at middle portions of the porous medium, and will be able to pass throughout the charged fiber network. Experiments confirm this; even in this case, some of the bacteria are physically trapped in the 3D fiber network, as shown in FIG. 4, which illustrates an experiment in which the unmodified glass was naturally negatively charged. If the bacteria are charged positively, then we use a negatively charged trapping material as shown in FIG. 2.

In view of the present invention, the "novel structural" feature of the activated microfibers is that they have a covalently coupled monolayer of positive (or negative) charge throughout a 3D network. This monolayer of charged molecules is chemically inert and remains stable over a wide range of pH>6, salinity conditions, and harsh environments, such as fuels. This configuration creates continually linked porous voids throughout the 3D network so that a contaminated liquid can pass through the filter network rapidly without a need for much excess pressure. At the same time, it is able to capture bacteria with the efficiency of a ~0.2-μm filter, because of the coulomb attraction, without being clogged as a result of large volumes of liquid passing through it. The presence of high concentrations of negative ions, such as chlorine ions ($Cl^-$) in the solution (e.g. seawater), has no effect on the BiyoTrap's ability to trap and concentrate bacteria because of the collective motion of the large body of bacterial surface charge repelling the small ions in solution.

Figure 2:
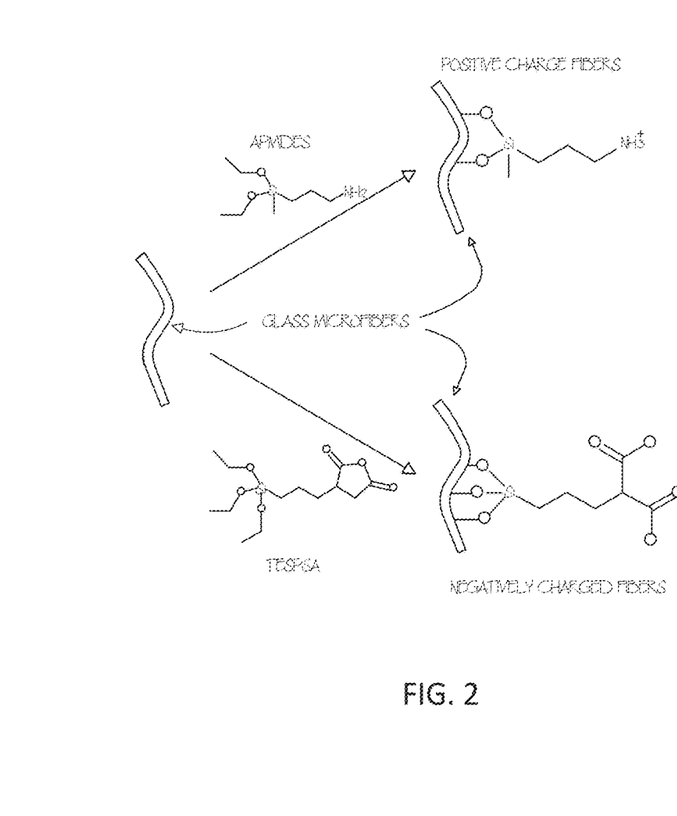
FIG. 2 represents the covalent coupling of the charged molecules to the glass microfibers.

FIG. 2 shows that this chemistry involves coupling aminosilane groups, such as 3-aminopropyl methyldiethoxysilane (APMDES) or carboxylated groups in 3-triethoxysilyl propylsuccinicanhydride (TESPSA), to the —OH-bearing moieties on the surfaces of glass microfibers (or other microfibers, such as cellulose). This produces a positive or negative layer of charged amines or carboxylate groups, respectively, on the 3D network of glass or other fibers.

In another embodiment, the present invention involves aminosilanes or other silanes of interest. The formerly mentioned surface modification could be attained, depending upon the silanes, through solution or vapor phase techniques. The process typically allows the deposition of 3-(aminopropyl)triethoxysilane (APTES) and TESPSA in solution by exposing the glass fibers to the vapors of APMDES by pulling a vacuum on liquid APMDES to generate the vapor phase (though the solution chemistry works equally well for the APMDES application when necessary). The modification (or activation) of microfiber surfaces is not trivial; it can easily be done poorly. Proper modification is absolutely crucial for bacteria trapping, and this needs to be confirmed rigorously.

X-ray photoelectron spectroscopy (XPS) is used to verify the surface monolayer properties of the modified microfibers, while zeta potential measurements are used to verify the surface charge concentrations of the microfibers. Glass fiber surfaces need to be cleaned by being heated to 120° C. or higher and exposed to UV ozone to remove environmental organic molecules from the surfaces of the microfibers, and to generate active —OH moieties on the surfaces of the 3D fibers for the silane groups to attach to. After modification, microfibers need to be heated at ~110° C. for about 1 h to remove non-covalently bound molecules from the surface.

Figure 3:
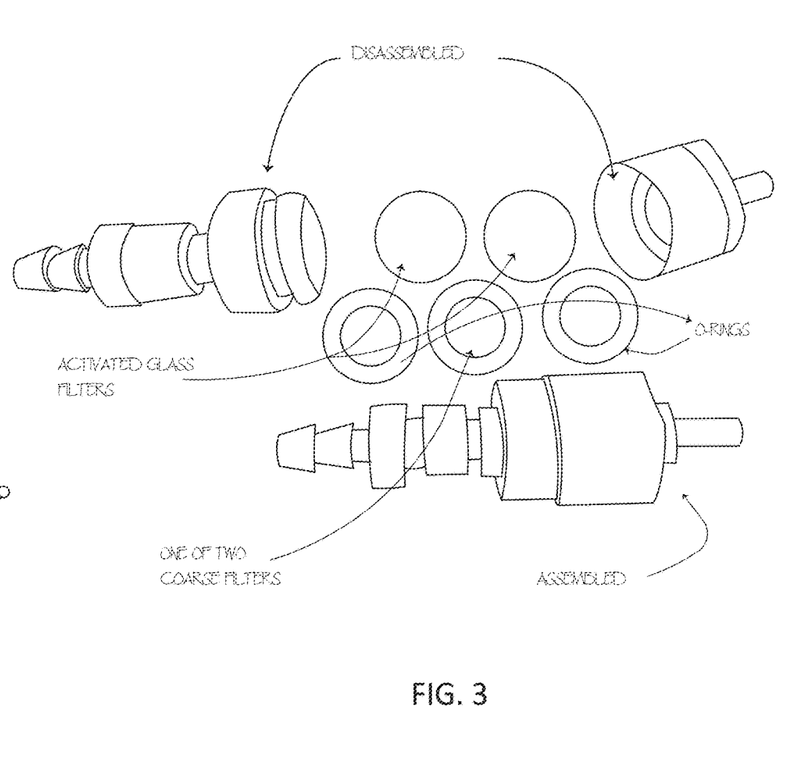
FIG. 3 shows the parts of the BiyoTrap, according to the preferred embodiment of the present invention.

The dimensions of the BiyoTrap can vary depending on the application. For example, if it is part of a handheld device with a cylindrical shape, it may have a ~5-6-mm inner diameter, a ~10-mm length, and a ~200-µL concentration volume. It could also be a part of a much larger BiyoTrap, such as a fuel quality monitoring system. This could be a cylindrical volume with a ~1-cm inner diameter, a ~2-3-cm length, and a ~2-mL concentration volume capable of handling tens of liters of trace contaminated liquid. If it is a bacteria removal filtration system, the actual areas of activated microfiltration material can exceed 1 square meter. The tested scaled-down versions of such BiyoTrap geometry are shown in FIG. 3, and are also shown schematically in FIG. 1C. In these systems, activated commercial glass and other fiber filter sheets that have a ~200-500 µm thickness have been used for this purpose. The activation of these filters must be performed. A stack of circularly cut sheets of these filters or a small amount of activated filter medium serves as the layered or packed BiyoTrap material, which is placed in the filter housings, as shown in FIG. 3.

FIG. 3 shows both the parts of the BiyoTrap and the assembled trap. Typically, a stack of 3-5 activated filter fibers or 37 mg of fiber material is used. Coarse metal filters are placed before and after the stack to hold the activated glass filters in place O-rings ensure that there is no leakage.

In reference to the invention, FIG. 4 depicts a graphical representation of the trapping experiment with *Marinobacter* in seawater. FIG. 4 also shows the trapping capacity of inactivated glass microfibers. As seen in FIG. 4, inactivated glass fibers release the majority of the bacteria into the effluent. Seawater contaminated with *Marinobacter* would easily attain the flow rate of 50 mL/min, and has the potential to flow at an even faster rate.

The present concept uses ATP bioluminescence as the rapid detection assay. This can be changed to a DNA assay or modified for better implementation of an ATP assay. ATP assays, though insensitive to DNA content, can easily give false positives, particularly in detecting trace concentrations of bacteria; this should be examined cautiously. For this reason, a well-thought-out control experiment must accompany each assay. In the present case, a small volume of a filter-sterilized version of the contaminated liquid can be passed through a second BiyoTrap to ascertain the background reading of the filter-sterilized medium in order to compare the actual reading with the background reading and thereby reveal the true level of bacterial contamination.

Figure 5:
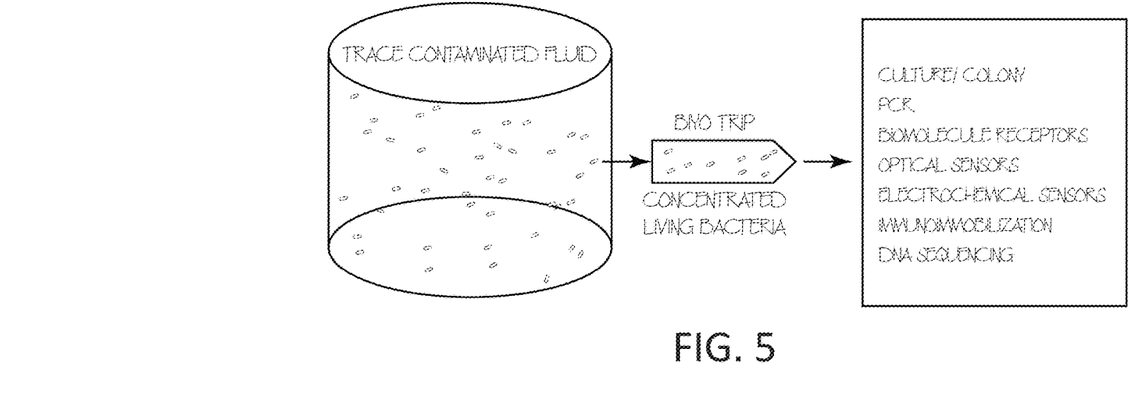
FIG. 5 is a schematic representation of the functioning of the BiyoTrap setup, according to the preferred embodiment of the present invention.

In FIG. 5, the schematic representation illustrates another aspect of the BiyoTrap system: the concentration of a pathogen from levels below the current detection limits to a level where detection is feasible through multiple methods which have the potential for differentiation between specific and nonspecific living bacteria.

According to the preferred embodiment of the present invention, the overall system is designed with the charged 3D network of microfibers, which are robust and comprise the inert surfaces. These microfibers can stay charged in a wide range of harsh chemical environments. Some amine groups can be permanently charged (such as quaternary amines) and are guaranteed to stay charged in harsh environments, such as fuels or contaminated sewer systems with copious amounts of dissolved hydrogen sulfide gas ($H_2S$). Furthermore, a monolayer of a charged silane group prevents other organics from physical adsorption or chemisorption on the surface of these fibers, enabling charged activity for a long period of time (months if not longer).

Figure 7:
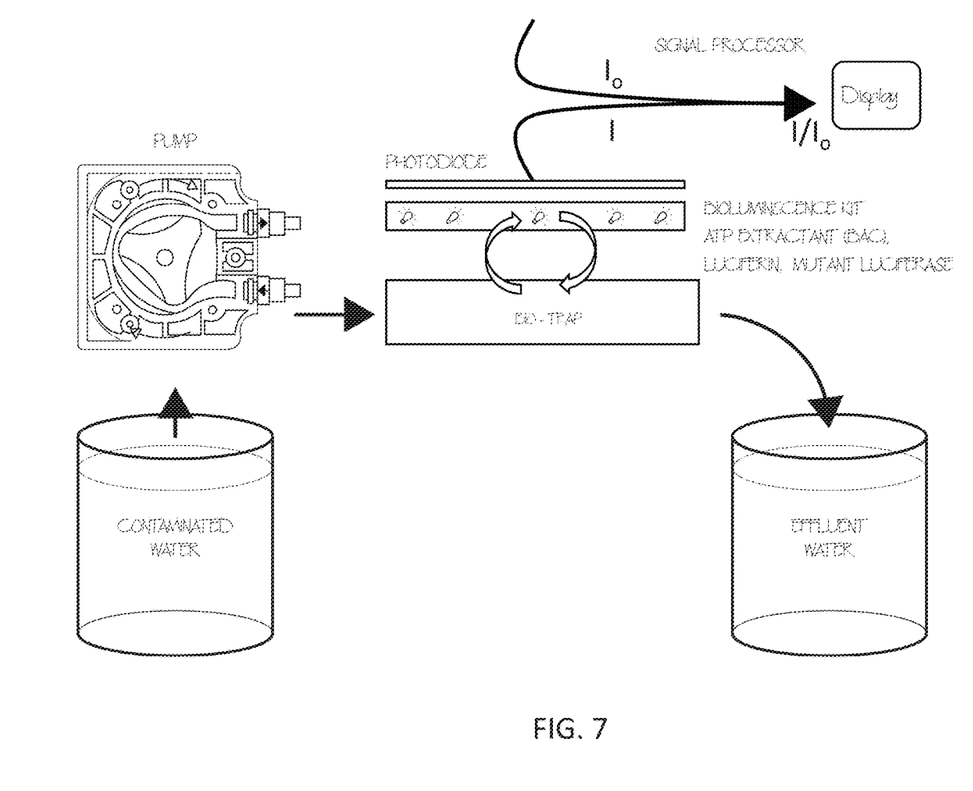
FIG. 7 is a schematic representation of a handheld trace bacteria sensor, according to the preferred embodiment of the present invention.

FIG. 7 is a schematic representation of a field-deployable bacterial detector based on the BiyoTrap concept. The lines connecting contaminated liquid, pump, BiyoTrap (a replaceable cartridge) and effluent are the most important component of the detector, where the actual concentration of the bacteria (or DNA) from a large volume of suspected liquid take place. The pump passes a large volume (e.g., liters) of contaminated fluid through the BiyoTrap in a short time (<1 hr) to concentrate the bacterial content of the contaminated liquid into a very small volume (~200-300 microliters) of the BiyoTrap. The bioluminescence kit shown on FIG. 7 facilitates mixing ATP extractant, luciferin, and lucifrace into the BiyoTrap so that the bacteria lyse and ATP is released into the solution. The ATP-rich solution is then pumped into the transparent container (marked with light bulbs) in front of a wide-array photo diode so that the optical signal due to bioluminescence can be recorded. Optical signal I is proportional to ATP concentration released. The optical signal from the photodiode, labeled as "I", is fed into a signal processor. A similar control signal labeled "Io" is fed into the signal processor from a module identical to the one described above using the same liquid but all the bacteria are removed from suspected liquid by filter sterilization (inserting a 0.1 µm filter into the line). In this case only a small volume (~1 mL) of filter sterilized liquid is used.

A display gives the ratio of the two signals, I/Io, as the degree of microbial contamination in the suspected liquid.

Figure 8:
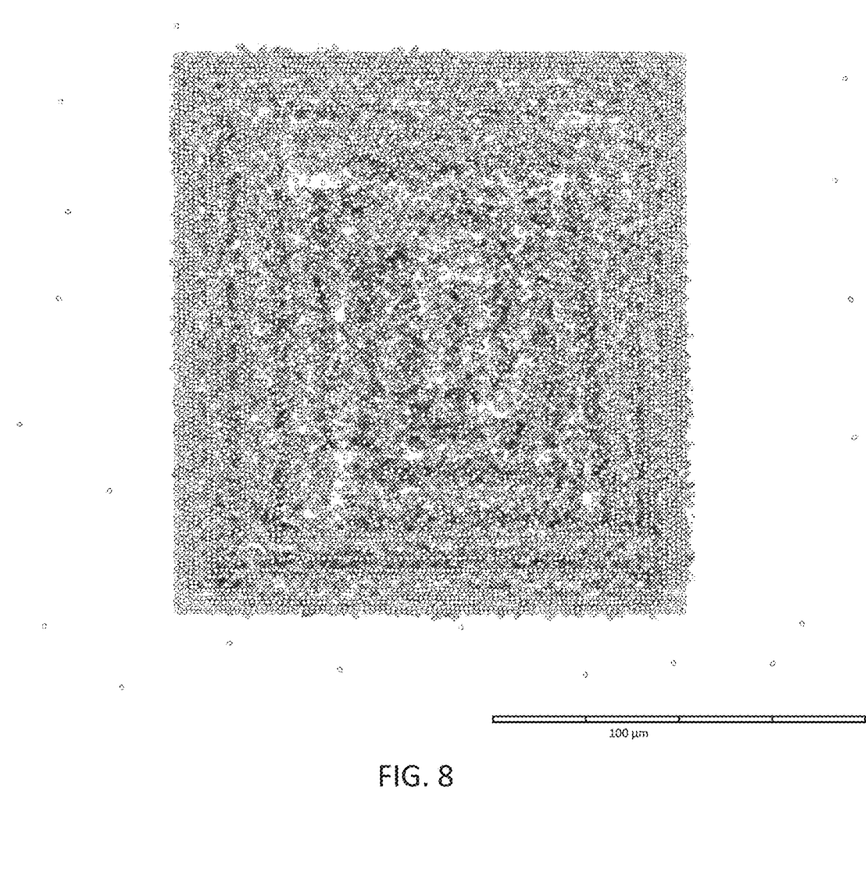
FIG. 8 shows immunoimmobilized *E. coli* on a silicon wafer.

Another means of detecting and identifying specific bacteria is their immobilization by means of antibodies raised against specific surface antigens (such as pili or lipopolysaccharides) of the targeted bacteria. The capture and immobilization of specific bacteria by antibody-antigen interactions is called immunoimmobilization. This was developed in our laboratories, and has been widely published. FIG. 8 shows *E. coli* immunoimmobilized by means of a specific antibody raised against its pili. Specific antibodies are either covalently attached to glass microfibers, or to the flat surfaces of glass or silicon wafers. Flat surfaces can be used for sorting, identifying, and culturing specific bacteria from a mixed population harvested from the BiyoTrap, while antibody-activated microfibers can be used in the BiyoTrap instead of charged microfibers to capture and concentrate specific pathogens by means of immunoimmobilization.

The BiyoTrap is expected to find a wide variety of applications, including the rapid detection of trace bacteria in contaminated liquids and in vegetable, fruit, meat, tabletop and countertop wash-offs and in the filtration of liquids (water or fuels) to remove bacteria or other microorganisms. It could be a front-end device for many conventional detection technologies, as shown in FIG. 5.

Briefly, the BiyoTrap has two steps: concentration and detection. The invention combines these two ideas into one innovative system to provide a handheld field-deployable bacterial sensor.

It is to be understood that the above description is intended to be illustrative, and not restrictive. For example, the above-discussed embodiments may be used in combination with each other. Many other embodiments will be apparent to those skilled in the art upon reviewing the above description.

The benefits and advantages which may be provided by the present invention have been described above with regard to specific embodiments. These benefits and advantages, and any elements or limitations that may cause them to occur or to become more pronounced, are not to be construed as critical, required, or essential features of any or all of the embodiments.

While the present invention has been described with reference to particular embodiments, it should be understood that the embodiments are illustrative, and that the scope of the invention is not limited to these embodiments. Many variations, modifications, additions, and improvements to the embodiments described above are possible. It is contemplated that these variations, modifications, additions, and improvements fall within the scope of the invention.

I claim:

1. A device for isolating negatively charged microorganisms and genetic material from a solution, the device comprising a 3-dimensional network of activated glass microfibers, wherein the glass microfibers define a series of continually linked voids within the 3-dimensional network, wherein the 3-dimensional network has a porosity of 80-90%, wherein a surface of each glass microfiber comprises a monolayer of positively charged but chemically nonreactive stable molecules, wherein the positively charged molecules are covalently bound to the glass microfiber surfaces, wherein, as the solution passes through the 3-dimensional network, an electrostatic coulomb attraction between the negatively charged microorganisms and genetic material and the positively charged molecules traps the negatively charged microorganisms and genetic material inside the voids, wherein a remainder of the solution passes through the 3-dimensional network.

2. The device of claim 1, wherein the positively charged molecules are APMDES molecules, wherein the APMDES molecules are bound to —OH moieties of the glass microfiber surfaces.

3. The device of claim 1, wherein a collective motion of the negatively charged microorganisms and genetic material prevents small negatively charged ions from bonding to the monolayer of positively charged molecules, wherein the negatively charged microorganisms and genetic material repel and sweep away the small negatively charged ions, wherein the small negatively charged ions pass through the 3-dimensional network.

4. The device of claim 1, further comprising a pump, wherein the pump pumps the solution through the 3-dimensional network.

5. The device of claim 4, wherein the device is a handheld device having a concentration volume of approximately 200-300 µL.

6. The device of claim 4, further comprising:
 a. a filter housing in communication with the pump;
 b. metal filters; and
 c. o-rings,
 wherein the glass microfibers, the metal filters, and the o-rings are positioned within the filter housing, wherein the glass microfibers are positioned between the metal filters, and wherein the o-rings are positioned at each end of the interior of the filter housing.

* * * * *